United States Patent [19]
Kulkarni et al.

[11] Patent Number: 5,994,533
[45] Date of Patent: Nov. 30, 1999

[54] PROCESS FOR THE RECOVERY OF TARTARIC ACID AND OTHER PRODUCTS FROM TAMARIND PULP

[75] Inventors: Mohan Gopalkrishna Kulkarni; Sudhir Sharadchandra Kulkarni; Sanjay Narayan Nene; Madhav Jagannath Thakar; Bhaskar Ganapatrao Gaikwad, all of Maharashtra, India

[73] Assignee: Council of Scientific & Industrial Research, New Delhi, Ind.

[21] Appl. No.: 08/907,891

[22] Filed: Aug. 11, 1997

[51] Int. Cl.$^6$ ........................................ C07H 1/08
[52] U.S. Cl. ........................ 536/128; 536/124; 536/127
[58] Field of Search ................................ 536/124, 114, 536/127, 128

[56] References Cited

PUBLICATIONS

Encyclopedia of Chemical Technology, 4th ed., vol. 13, pp. 1071–1078, 1995.
Encyclopedia of Chemical Technology, 1st ed., vol. 13, pp. 645–656, 1963.
National Manufacturing LTD, Product Guide–Canned Drinks.

*Primary Examiner*—James O. Wilson
*Assistant Examiner*—Howard Owens
*Attorney, Agent, or Firm*—Birch, Stewart, Kolasch & Birch, LLP

[57] ABSTRACT

The invention provides Potassium bitartrate, pectin, L(+) tartaric acid and fruit sugars present in tamarind pulp, which are recovered sequentially by extracting the pulp in water, concentrating and chilling the extract, filtering out potassium bitartrate, precipitating out pectin from the filtrate by addition of acetone, extracting L(+) tartaric acid selectively by complexation with tertiary amine and recovering from the amine layer by back extraction into aqueous layer in the presence of a diluent at around 70° C. followed by concentration and drying of the aqueous layer and treating the raffinate layer from solvent extraction with activated carbon, anion exchange resin, and concentrating to yield sugar containing 70% sugars.

10 Claims, No Drawings

PROCESS FOR THE RECOVERY OF TARTARIC ACID AND OTHER PRODUCTS FROM TAMARIND PULP

FIELD OF THE INVENTION

This invention relates to an improved process for the recovery of tartaric acid and other products from tamarind pulp. More particularly, it relates to the sequential recovery of potassium bitartrate, pectin, tartaric acid and fruit sugar, from the tamarind pulp.

1. Background of Invention

Tartaric acid is a dihydroxy dicarboxylic acid which exists in an optically active form, as a racemic mixture, and also in meso form. The product finds wide range of applications in food industry, in baking industry and in electro chemical industry. In pharmaceutical industry it finds applications as effervescent compound. Its most important application in pharmaceutical industry is in the racemic resolution of chiral compounds such as phenyl glycine, naproxen, ethambutol etc. Amongst various forms of tartaric acid, (L+) tartaric acid is the only product most suitable for applications in racemic resolution. It is therefore the most important form of tartaric acid of commercial importance. Consequently a number of attempts have been made in the past to recover tartaric acid from natural resources and/or synthesize tartaric acid in optically pure L(+) form. But no successful attempt has so far been made to recover L(+) tartaric acid from natural sources other than wine argols nor by synthetic routes, as is evident from the fact that even today wine argols is the only source for the recovery of L(+) tartaric acid (G T Blair and J J Defraties in Kirk-Othomer Encyclopedia of Chemical Technology, fourth edn., vol 13, p. 1042, 1995, John Wiley & Sons, New York).

2. Description of the Prior Art

Conventionally, tartaric acid has been recovered from wine argols by converting it into calcium salt of tartaric acid and subsequent treatment with sulphuric acid to recover tartaric acid (G T Blair and J J De Fraties in Kirk Othmer, Encyclopedia of Chemical Technology, Fourth Edn., vol 13, p. 1042, 1995, John Wiley & Sons, New York; J W Black, The industrial Chemist, November 1938, p.443-; J W Black, The Industrial Chemist, December 1938, p.521). However, one of the drawbacks of this process is that it generates calcium sulphate as undesirable byproduct.

The synthetic method for the manufacture of tartaric acid by epoxidation of maleic acid and subsequent treatment with hydrogen peroxide in the presence of tungsten based catalyst leads to racemic mixture and also formation of calcium sulphate as byproduct. However, as mentioned earlier, the most desirable form of tartaric acid is L(+) tartaric acid.

Subsequently L (+) tartaric acid has been produced in high efficiency from cis epoxy succinic acid by microorganisms belonging to the family of pseudomonas to yield L(+) tartaric acid (U.S. Pat. No. 4,011,135 (1977); U.S. Pat. No. 4,013,509 (1976)). However, this method does not seem to be commercially practiced because of economic reasons.

Tamarind (tamarindus indica) is a widely grown tree found in the tropical countries the fruits of which contain as much as 10–15% of L (+) tartaric acid; fruit sugar 36–38%, and pectin 2.4–4.4% depending upon the source of origin and the stage of maturation of the fruit (Tamarindus Indica, in Wealth of India, Y H Chadha Ed. Vol 10, p.114, 1976, Council of Scientific & Industrial Research, New Delhi). It therefore is a potential source for the recovery of tartaric acid, pectin, potassium bitartrate and fruit sugar. Efforts to recover tartaric acid from tamarind pulp in the past have been based on treatment of pulp extract with calcium hydroxide and subsequent acidification of calcium tartarate, which generates tartaric acid and calcium sulfate (J W Black, The Industrial Chemist, November 1938, p. 443-; J W Black, The Industrial Chemist, December 1938, p. 521; J W Black, The Industrial Chemist, March 1939, p. 100). This method suffers from the drawback that pectin also precipitates in the form of calcium pectate which is extremely difficult to separate from calcium tartarate. Alternatively, L(+) tartaric acid has also been recovered from the tamarind pulp by aqueous extraction followed by treatment with ion exchange resins. Ion exchange methods adopted in the past suffer from the limitation that rapid fouling of the columns takes place making the recovery of the tartaric acid economically unattractive (R P Shukla, J Ind Chem Soc Ind & News, 20 (3&4), 135 (1957)). This is because other ingredients present in the tamarind pulp which can foul the column are not removed prior to the ion exchange treatment.

In our co-pending patent application No. 857/ DEL/96, we have described and claimed, an improved process for the recovery of potassium bitartrate, pectin, tartaric acid and sugar. As a result of further research by us in this area, the said process has been considerably improved by us to simplify the process and to improve the product quality.

In the process developed by us, four commercially important constituents of the tamarind pulp, potassium bitartrate, pectin, tartaric acid and fruit sugar, are sequentially recovered from the tamarind pulp. The process developed by us has the following advantages. It enables recovery of four products of commercial value from tamarind pulp, a raw material abundantly and cheaply available in tropical countries and not hitherto commercially exploited for the recovery of potassium bitartrate, tartaric acid, pectin and fruit sugar. As a result, the process becomes economically more competitive compared to conventional process which recovers only tartaric acid and potassium bitartrate from wine argols, which being available in limited quantities, limits the availability of tartaric acid (Chemical Marketing Reporter, Aug. 28, 1995, p.1 and Sep. 23, 1996, p.6). The sequence of recovery of each of the product is such that recovery of each product simplifies the process of recovery of the product being subsequently recovered. Each product is recovered in high purity as to meet the specifications of the food and pharmaceutical industry. Finally, in the process developed earlier, tartaric acid is first recovered as calcium tartaric from which tartaric acid is obtained by acidification along with calcium sulphate as the byproduct which poses waste disposal problems. In contrast, the process developed by us does not produce any byproducts. Also, the process uses a tertiary amine for extraction without any chlorinated or oxygenated solvent for the extraction of tartaric acid from aqueous solution. This eliminates, avoids hazards associated with the handling of such solvents and makes the process more environment friendly, and eliminates the makes the solvent recovery step which makes the process simpler and economical.

OBJECT OF THE INVENTION

The object of the present invention is to provide a process for the recovery of Tartaric Acid and other products particularly, Potassium bitartrate, Pectin, and Fruit sugar from tamarind pulp, improving the quality of the products and also to provide a simplified, economical and environmental-friendly process.

SUMMARY OF THE INVENTION

To achieve the above object, the present invention provides a process thereby Potassium bitartrate, pectin, L(+)

tartaric acid and fruit sugars present in tamarind pulp are recovered sequentially by extracting the pulp in water, concentrating and chilling the extract, filtering out potassium bitartrate, precipitating out pectin from the filtrate by addition of acetone, extracting L(+) tartaric acid selectively by complexation with tertiary amine and recovering from the amine layer by back extraction into aqueous layer in the presence of a diluent at around 70° C., followed by concentration and drying of the aqueous layer and treating the raffinate layer from solvent extraction with activated carbon, anion exchange resin, and concentrating to yield a fruit sugar containing 70% sugars.

DETAILED DESCRIPTION OF THE INVENTION

Accordingly, the present invention provides a process for the recovery of Tartaric acid and other products particularly, Potassium bitartrate, Pectin, Tartaric acid and Fruit sugar from the Tamarind pulp, which comprises:

i) extracting Tamarind pulp using 1:1 to 1:8 volumes of water at a temperature in the range of 25 to 100° C. in any conventional stirred vessel equipment for about 0.5–6 hrs to obtain a mixture of tartaric acid, potassium bitartrate, pectin and fruit sugar in aqueous medium in quantitative manner;

ii) separating the residue from the pulp extract, treating the aqueous extract with a decolourising agent, for a period in the range of 10 mins. to 90 mins. at a temperature in the range 20° C. to 80° C., stirring the mixture for 0.5 to 2 hrs at a temperature in the range of 20 C.–50° C., further treating the aqueous extract with decolourising agent and filtering it to remove the colouring matter, separating and concentrating the filtrate to recover the maximum amount of potassium bitartrate, concentrating the filtrate further to reduce the volume to ½ to ¹⁄₁₀th of the original volume, at a temperature in the range of 60° to 90° C. under reduced pressure, cooling the concentrated pulp allowing the concentrated pulp to stand to bring about complete separation of potassium bitartrate and subsequently purifying potassium bitartrate by recrystallization;

iii) treating the mother liquor obtained in step (ii) with an organic solvent to precipitate pectin, purifying the resultant pectin by repeated washing with acidified solvent;

iv) evaporating the solvent from both the filtrate and pectin washings obtained from step (ii), treating the abovesaid filtrate with a cation exchanger resin in H form, and extracting the eluate with a tertiary amine, separating the amine layer containing tartaric acid and diluting with a diluent and water and simultaneously heating the mixture at a temperature in the range of 50° C.–80° C., allowing the aqueous layer to separate and the aqueous layer containing tartaric acid, treating with decolourising agent under constant stirring for a time in the range of 10 to 60 mins, passing the filtrate through a microporous adsorbent of the type Rohm and Haas XAD 7 or its equivalent, evaporating the solvent and drying the aqueous solution to get solid tartaric acid, and v) injecting the aqueous raffinate solution from step (iv), which is rich in fruit sugar and containing small amounts of tartaric acid with steam for a period in the range of 5 to 40 mins., followed by treatment with decolourising agent, removing the decolourising agent and passing the filtrate over an anion exchange resin, concentrating the eluate obtained from the column under vacuum at a temperature in the range of 55–60° C. to yield an aqueous solution of fruit sugar.

EMBODIMENTS OF THE INVENTION

In an embodiment of the present invention, the water used for extracting the tamarind pulp may be such as natural water, distilled water, or demineralised water.

In another embodiment, the decolourising agent used in step (ii) may be selected from sulphur dioxide ($SO_2$), sodium hydrosulphite, or activated carbon.

In yet another embodiment the treatment with $SO_2$ may be carried out for a period ranging between 10 to 90 minutes preferably 15 to 60 minutes and most preferably 20 to 40 minutes.

In still another embodiment the treatment of the $SO_2$ may be carried out at a temperature ranging between 20 to 80° C. preferably 30 to 60° C. and most preferably 40 to 60° C.

In still another embodiment, the quantity of sodium hydrosulphite may be in the range of 0.5 to 5.0%, preferably 0.5 to 3.0% and most preferably 1 to 2%

In yet another embodiment, the treatment of sodium hydrosulphite may be done under constant stirring for a period ranging between 0.5 to 2 hrs.

In yet another embodiment the treatment with sodium hydrosulphite may be done at a temperature ranging between 20 to 50° C., preferably 25 to 40° C., most preferably 30 to 35° C.

In yet another embodiment of the present invention, the solvent used in step (iii) for precipitating the pectin may be selected from iso propanol, acetone methyl ethyl ketone, or mixtures of acetone and water or methyl ethyl ketone and water in the proportions between 90:10 to 98:2, which enables recovery of pectin from the aqueous solution in a fibrous form, minimizing the entrapment of tartaric acid and sugar in the pectin.

In yet another embodiment of the present invention, the amount of solvent used in step (iii) is in the range of 0.5 to 5.0 times the volume of aqueous pectin solution.

In yet another embodiment, the acidified solvent used to wash the pectin may be selected from methanol, ethanol, isoprapanol, acetone methyl, ethyl ketone or with methanol, ethanol, isopropanol, acetone, methyl ethyl ketone containing no free acid with mixture of water with either methanol, ethanol, isopropanol, acetone or methyl ethyl ketone.

In another embodiment the ratio of tertiary amine to tartaric acid in step (iii) may be 0.5 to 6, preferably 0.75 to 4, and most preferably 1–3 moles.

In yet another embodiment, the tertiary amine is directly used in the extraction of the tartaric acid.

In yet another embodiment the ratio of the diluent used in step (iv) to the amine layer may be 3 to 10, preferably 4–8 and most preferably 4.5 to 6 parts of n-hexane per part of amine layer by volume and with 0.25 to 4, preferably 1 to 3 and most preferably 0.4 to 1.5 parts of water in one to three stages.

In yet another embodiment, the mixture containing tertiary amine, tartaric acid, water and n-hexane may be treated to 70° C., preferably 65° C. most preferably upto 60° C.

In yet another embodiment the carbon added in step (iv) may be in 0.5% to 3%, preferably 2–3% and most preferably 1–2% by w/w of the aqueous solution of tartaric acid.

In yet another embodiment of the invention, the tertiary amine used in step (iv) may be such as trioctylamine, tridodecylamine, trilaurylamine and/or mixture thereof.

In a feature of the present invention, potassium bitartrate, pectin, tartaric acid and sugar are sequentially recovered from the tamarind pulp extract as to meet the high purity levels needed in the pharmaceutical and food industry. Further, recovery of each product simplifies the process of recovery of the product being recovered subsequently, Thus, recovery of potassium bitartrate eliminates the presence of the bitartrate as an impurity in products being recovered subsequently. Recovery of pectin by precipitation simplifies the recovery of tartaric acid from aqueous solutions using tertiary amines as the extractant. Finally, recovery of potassium bitartrate, pectin, and tartaric acid, leaves behind an aqueous solution of glucose and fructose which can find applications as a sweetener in food industry.

In another feature of the present invention a fruit sugar solution containing 40 to 44% fructose, 32 to 35% glucose and free from tartaric acid and pectin is obtained from tamarind pulp.

The process of the present invention is described hereinbelow with reference to examples which are illustrative only and should not be construed to limit the scope of the present invention in any manner.

EXAMPLE 1

500 gms of tamarind pulp was extracted for one hr with 2 l water, at 75° C., another 2 l of water at 70° C. was added and extraction continued for another hour. The suspension was filtered and the filtrate was mixed with 40 gms activated charcoal, stirred for 15 min. at 70° C. and filtered to remove activated charcoal. The filtrate was centrifuged to obtain a clear solution. This was vacuum concentrated at 50° C. to reduce the volume to 400 ml. The concentrate was then cooled to 10 ° C. and allowed to stand for 4 hrs. The salt precipitated was recovered by filtration. The residue was washed with 2 aliquots of 50 ml of water at 5° C. and washings added to the filtrate. The residue was recrystallized from hot water at 70° C. to yield 18 gm potassium bitartrate having purity >99%.

The filtrate obtained after removal of potassium bitartrate was mixed with one l of methanol and stirred for 30 min. The pectin precipitated was washed with 500 ml methanol water mixture and washings added to the filtrate. The pectin was dried with methanol and then dried in oven at 50° C. under vacuum to yield 15 gm pectin.

The filtrate obtained after recovery of pectin was vacuum concentrated to recover methanol completely, passed through strong cation exchange resin in H form and extracted with 200 gms of tri octyl amine. After extraction the amine, layer containing tartaric acid was diluted with 4 parts of n-hexane per part of amine layer. Then to this mixture 0.25 parts of water per part of amine layer was added. Then, extraction of tartaric acid was done in aqueous layer at 50° C. in three stages. The aqueous layer was collected and activated carbon was then added. The mixture was stirred vigorously and filtered to obtain a clear solution. Then the solution was passed through a macroporous adsorbent of the type Rohm and Haas XAD7 or its equivalent. Then the resulting tartaric acid solution was vacuum dried at 60° C. to yield 35 gms tartaric acid.

The aqueous solution of raffinate obtained after extraction of tartaric acid with trioctyl amine, was given steam treatment for 15 min. The activated carbon was then added, the mixture stirred vigorously aid filtered to obtain a clear solution. Then she solution was passed through strong anion exchange resin in OH form and then concentrated by vacuum evaporation to a sugar content of 65%.

EXAMPLE 2

500 gms of tamarind pulp was extracted for one hr with 1.5 l water, at 80° C., another 2 l of water at 80° C. was added and extraction continued for another hour. The suspension was filtered and the filtrate was mixed with 80 gms activated charcoal stirred for 30 min. at 70° C. and filtered to remove activated charcoal. The filtrate was centrifuged to obtain a clear solution. This was vacuum concentrated at 60° C. to reduce the volume to 775 ml. The concentrate was then cooled to 15° C. and allowed to stand for 4 hrs. The salt precipitated was recovered by filtration. The residue was washed with 2 aliquots of 50 ml of water at 5° C. and washings added to the filtrate. The residue was recrystallized from hot water at 70° C. to yield 19 gm of potassium bitartrate, having purity >99%

The filtrate obtained after removal of potassium bitartrate was mixed with one l of acetone and stirred for 45 min. The pectin precipitated was washed with 600 ml acetone water mixture and washings added to the filtrate. The pectin was dried with acetone and then dried in oven at 50° C. under vacuum to yield 14 gm pectin.

The filtrate obtained after recovery of pectin was vacuum concentrated to recover acetone completely, passed through strong cation exchange resin in H form and extracted with 220 gms of tri octyl amine. After extraction the amine layer containing tartaric acid was diluted with 5 parts of n-hexane per part of amine layer. Then to this mixture 1.25 parts of water per part of amine layer was added. Then, extraction of tartaric acid was done in aqueous layer at 55° C. in three stages. The aqueous layer was collected and activated carbon was then added. The mixture was stirred vigorously and filtered to obtain a clear solution. Then the solution was passed through a macroporous adsorbent of the type Rohm and Haas XAD7 or its equivalent. Then the resulting tartaric acid solution was vacuum dried at 55° C. to yield 36 gms tartaric acid.

The aqueous solution raffinate obtained after extraction of tartaric acid with trioctyl amine was given steam treatment for 20 min. The activated carbon was then added, the mixture stirred vigorously and filtered to obtain a clear solution. Then the solution was passed through a strong anion exchange resin in OH form and then concentrated by vacuum evaporation to a sugar content of 65%.

EXAMPLE 3

500 gms of tamarind pulp was extracted for one hr with 2 l water, at 60° C., another 2 l of water at 60° C. was added and extraction continued for another hour. The suspension was filtered and the filtrate was mixed with 60 gms activated charcoal, stirred for 25 min. at 70° C. and filtered to remove activated charcoal. The filtrate was centrifuged to obtain a clear solution. This was vacuum concentrated at 60° C. to reduce the volume to 500 ml. The concentrate was then cooled to 5° C. and allowed to stand for 10 hrs. The salt precipitated was recovered by filtration. The residue was washed with 2 aliquots of 50 ml of water at 5° C. and washings added to the filtrate. The residue was recrystallized from hot water at 70° C. to yield 20 gm of potassium bitartrate, having purity >99%.

The filtrate obtained after removal of potassium bitartrate was mixed with 1.5 l of ethanol and stirred for 30 min. The pectin precipitated was washed with 700 ml ethanol water mixture and washings added to the filtrate. The pectin was dried with ethanol and then dried in oven at 50° C. under vacuum to yield 16 gm pectin.

The filtrate obtained after recovery of pectin was vacuum concentrated to recover ethanol completely, passed through strong cation exchange resin H form and extracted with 180 gms of tri octyl amine. After extraction, the amine layer containing tartaric acid was diluted with 3 parts of n-hexane per part of amine layer. Then to this mixture 0.75 parts of water per part of amine layer was added. Then, extraction of tartaric acid was done in aqueous layer at 65° C. in three stages. The aqueous layer was collected and activated carbon was then added. The mixture was stirred vigorously and filtered to obtain a clear solution. Then the solution was passed through a macroporous absorbent of the type Rohm & Haas XAD7 or its equivalent. Then the resulting tartaric acid solution was vacuum dried at 60° C. to yield 34 gms tartaric acid.

The aqueous solution of raffinate obtained after extraction of tartaric acid with trioctyl amine was given steam treatment for 5 min. The activated carbon was then added, the mixture stirred vigorously and filtered to obtain a clear solution. Then the solution was passed through strong anion exchange resin in OH form and then concentrated by vacuum evaporation to a sugar content of 65%.

EXAMPLE 4

500 gms of tamarind pulp was extracted for one hr with 2 l water, at 30° C., another 2 l of water at 30° C. was added and extraction continued for another hour. The suspension was filtered and the filtrate was mixed with 35 gms activated charcoal, stirred for 15 min. at 70° C. and filtered to remove activated charcoal. The filtrate was centrifuged to obtain a clear solution. This was vacuum concentrated at 50° C. to reduce the volume to 550 ml. The concentrate was then cooled to 10° C. and allowed stand for 3 hrs. The salt precipitated was recovered by filtration. The residue was washed with 2 aliquots of 50 ml of water at 5° C. and washings added to the filtrate. The residue was recrystallized from hot water at 70° C. to yield 21 gm of potassium bitartrate, having purity >99%.

The filtrate obtained after removal of potassium bitartrate was mixed with 1.2 l of methanol and stirred for 40 min. The pectin precipitated was washed with 650 ml methanol water mixture and washings added to the filtrate. The pectin was dried with methanol and then dried in oven at 50° C. under vacuum to yield 15 gm pectin.

The filtrate obtained after recovery of pectin was vacuum concentrated to recover methanol completely, passed through strong cation exchange resin in H form and extracted with 190 gms of tri octyl amine. After extraction, the amine layer containing tartaric acid was diluted with 6 parts of n-hexane per part of amine layer. Then to this mixture 1.5 parts of water per part of amine layer was added. Then, extraction of tartaric acid was done in aqueous layer at 60° C. in three stages. The aqueous layer was collected and activated carbon was then added. The mixture was stirred vigorously and filtered to obtain a clear solution. Then the solution was passed through a macroporous adsorbent of the type Rohm and Haas XAD7 or its equivalent. Then the resulting tartaric acid solution was vacuum dried at 60° C. to yield 37 gms tartaric acid.

The aqueous solution of raffinate obtained after extraction of tartaric acid with trioctyl amine was given steam treatment for 25 min. The activated carbon was then added, the mixture stirred vigorously and filtered to obtain a clear solution. Then the solution was passed through strong anion exchange resin in OH form and then concentrated by vacuum evaporation to a sugar content of 65%.

EXAMPLE 5

500 gms of tamarind pulp was extracted in eight steps wit 1 l water, at 30° C., for half an hour each. The extracts were collected, mixed and filtered. The sulphur dioxide gas was passed through the extract for twenty min. at 30° C. and then the filtrate was mixed with 40 gms activated charcoal, stirred for 20 min. at 70° C. and filtered to remove activated charcoal. The filtrate was centrifuged to obtain a clear solution. This was vacuum concentrated at 65° C. to reduce the volume to 470 ml. The concentrate was then cooled to 12° C. and allowed to stand for 8 hrs. The salt precipitated was recovered by filtration. The residue was washed with 2 aliquots of 50 ml of water at 5° C. and washings added to the filtrate. The residue was recrystallized from hot water at 70° C. to yield 20 gm of potassium bitartrate, having purity >99%.

The filtrate obtained after removal of potassium bitartrate was mixed with one l of isopropanol and stirred for 30 min. The pectin precipitated was washed with 500 ml methanol water mixture and washings added to the filtrate. The pectin was dried with isopropanol and then dried in oven at 50° C. under vacuum to yield 17 gm pectin.

The filtrate obtained after recovery of pectin was vacuum concentrated to recover isopropanol completely, passed through strong cation exchange resin in H form and extracted with 200 gms of tri octyl amine. After extraction, the amine layer containing tartaric acid was diluted with 7 parts of n-hexane per part of amine layer. Then to this mixture 2 parts of water per part of amine layer was added. Then, extraction of tartaric acid was done in aqueous layer at 70° C. in three stages. The aqueous layer was collected and activated carbon was then added. The mixture was stirred vigorously and filtered to obtain a clear solution. Then the solution was passed through a macroporous adsorbent of the type Rohm and Haas XAD7 or its equivalent. Then the resulting tartaric acid solution was vacuum dried at 50° C. to yield 33 gms tartaric acid.

The aqueous solution of raffinate obtained after the extraction of tartaric acid with trioctyl amine was given steam treatment for 15 min. The activated carbon was then added, the mixture stirred vigorously and filtered to obtain a clear solution. Then the solution was passed through strong anion exchange resin in OH form and then concentrated by vacuum evaporation to a sugar content of 65%.

EXAMPLE 6

500 gms of tamarind pulp was extracted for one hr with 1 l water at room temperature and filtered. The residue was extracted with 1 l water at room temperature. The procedure was further repeated again for five times. All filtrates were mixed together and 80 gm activated charcoal was added. The suspension was stirred for 15 min at room temperature and filtered to remove activated charcoal. The filtrate was centrifuged to obtain a clear solution. This was vacuum concentrated at 50° C. to reduce the volume to 400 ml. The concentrate was then cooled to 14° C. and allowed to stand for 3 hrs. The salt precipitated was recovered by filtration. The residue was washed with 2 aliquots of 50 ml of water at 5° C. and washings added to the filtrate. The residue was recrystallized from hot water at 70° C. to yield 22 gm of potassium bitartrate, having purity >99%.

The filtrate obtained after removal of potassium bitartrate was mixed with 1.4 l of methanol water mixture and stirred for 45 min. The pectin precipitated was washed with 500 ml methanol water mixture and washings added to the filtrate. The pectin was dried with methanol and then dried in oven at 50° C. under vacuum to yield 15 gm pectin.

The filtrate obtained after recovery of pectin was vacuum concentrated to recover methanol completely, passed through strong cation exchange resin in H form and extracted with 170 gms of tri octyl amine. After extraction, the amine layer containing tartaric acid was diluted with 9 parts of n-hexane per part of amine layer. Then to this mixture 0.5 parts of water per part of amine layer was added. Then, extraction of tartaric acid was done in aqueous layer at 60° C. in three stages. The aqueous layer was collected and activated carbon was then added. The mixture was stirred vigorously and filtered to obtain a clear solution. Then the solution was passed through a macroporous adsorbent of the type Rohm and Haas XAD7 or its equivalent. Then the resulting tartaric acid solution was vacuum dried at 60° C. to yield 35 gms tartaric acid.

The aqueous solution raffinate of obtained after the extraction of tartaric acid with trioctyl amine was given steam treatment for 20 min. The activated carbon was then added, the mixture stirred vigorously and filtered to obtain a clear solution. Then the solution was passed through strong anion exchange resin in OH form and then concentrated by vacuum evaporation to a sugar content of 65%.

EXAMPLE 7

500 gms of tamarind pulp was extracted for one hr with 2 l water, at 75° C., another 2 l of water was added and extraction continued for another hour. The suspension was filtered and then sulphur dioxide gas was passed through the extract for 25 min. at 40° C. and then the filtrate was mixed with 40 gms activated charcoal, stirred for 15 min. at 70° C. and filtered to remove activated charcoal. The filtrate was centrifuged lo obtain a clear solutions. This was vacuum concentrated at 60° C. to reduce the volume to 425 ml. The concentrate was then cooled to 20° C. and allowed to stand for 4 hrs. The salt precipitated was recovered by filtration. The residue was washed with 2 aliquots of 50 ml of water at 5° C. and washings added to the filtrate. The residue was recrystallized from hot water at 70° C. to yield 21 gm of potassium bitartrate, having purity >99%.

The filtrate obtained after removal of potassium bitartrate was mixed with one l of methanol and stirred for 45 min. The pectin precipitated was washed with 500 ml methanol water mixture and washings added to the filtrate. The pectin was dried with methanol and then dried in oven at 50° C. under vacuum to yield 16 gm pectin.

The filtrate obtained after recovery of pectin was vacuum concentrated to recover methanol completely, passed through strong cation exchange resin in H form and extracted with 240 gms of tri octyl amine. After extraction, the amine layer containing tartaric acid was diluted with 6 parts of n-hexane per part of amine layer. Then to this mixture 3 parts of water per part of amine layer was added. Then, extraction of tartaric acid was done in aqueous layer at 50° C. in three stages. The aqueous layer was collected and activated carbon was then added. The mixture was stirred vigorously and filtered to obtain a clear solution. Then the solution was passed through a macroporous adsorbent of the type Rohm and Haas XAD7 or its equivalent. Then the resulting tartaric acid solution was vacuum dried at 60° C. to yield 34 gms tartaric acid.

The aqueous solution of raffinate obtained after the extraction of tartaric acid with trioctyl amine was given steam treatment for 10 min. The activated carbon was then added, the mixture stirred vigorously and filtered to obtain a clear solution. Then the solution was passed through strong anion exchange resin in OH form and then concentrated by vacuum evaporation to a sugar content of 65%.

EXAMPLE 8

500 gms of tamarind pulp was extracted for one hr with 1.5 l water, at 50° C., another 2 l of water at 50° C. was added and extraction continued for another hour. The suspension was filtered and then 30 g sodium hydrosulphite was added and stirred for 60 min. at 50° C. The filtrate was mixed with 20 gms activated charcoal, stirred for 30 min. at 50° C. and filtered to remove activated charcoal. The filtrate was centrifuged to obtain a clear solution. This was vacuum concentrated at 60° C. to reduce the volume to 775 ml. The concentrate was then cooled to 15° C. and allowed to stand for 4 hrs. The salt precipitated was recovered by filtration. The residue was washed with 2 aliquots of 50 ml of water at 5° C. and washings added to the filtrate. The residue was recrystallized from hot water at 70° C. to yield 19 gm of potassium bitartrate, having purity >99%.

The filtrate obtained after removal of potassium bitartrate was mixed with one l of acetone and stirred for 45 min. The pectin precipitated was washed with 600 ml acetone: water mixture and washings added to the filtrate. The pectin was dried with acetone and then dried in oven at 50° C. under vacuum to yield 14 gm pectin.

The filtrate obtained after recovery of pectin was vacuum concentrated to recover acetone completely, passed through strong cation exchange resin in H form and extracted with 220 gms of tri octyl amine. After extraction the amine layer containing tartaric acid was diluted with 5 parts of n-hexane per part of amine layer. Then to this mixture 1.25 parts of water per part of amine layer was added. Then, extraction of tartaric acid was done in aqueous layer at 55° C. in three stages. The aqueous layer was collected and activated carbon was then added. The mixture was stirred vigorously and filtered to obtain a clear solution. Then the solution was passed through a macroporous adsorbent of the type Rohm and Haas XAD7 or its equivalent. Then the resulting tartaric acid solution was vacuum dried at 55° C. to yield 36 gms tartaric acid.

The aqueous solution of raffinate obtained after extraction of tartaric acid with trioctyl amine was given steam treatment for 20 min. The activated carbon was then added, the mixture stirred vigorously and filtered to obtain a clear solution. Then the solution was passed through strong anion exchange resin in OH form and then concentrated by vacuum evaporation to a sugar content of 65%.

EXAMPLE 9

500 gms of tamarind pulp was extracted for one hr with 1.5 l water, at 80° C., another 2 l of water at 80° C. was added and extraction continued for another 2 hrs. The suspension was filtered and then 20 g hydrosulphite was added and stirred for 30 min. at 30° C. The filtrate was mixed with 40 gms activated charcoal, stirred for 30 min. at 70° C. and filtered to remove activated charcoal. The filtrate was centrifuged to obtain a clear solution. This was vacuum concentrated at 60° C. to reduce the volume to 800 ml. The concentrate was then cooled to 15+ C. and allowed to stand for 4 hrs. The salt precipitated was recovered by filtration. The residue was washed with 2 aliquots of 50 ml of water at 5° C. and washings added to the filtrate. The residue was recrystallized from hot water at 70° C. to yield 19 gm of potassium bitartrate, having purity >99%.

The filtrate obtained after removal of potassium bitartrate was mixed with 1 l of acetone and stirred for 45 min. The pectin precipitated was washed with 600 ml acetone: water mixture and washings added to the filtrate. The pectin was dried with acetone and then dried in oven at 50° C. wider vacuum to yield 14 gm pectin.

The filtrate obtained after recovery of pectin was vacuum concentrated to recover acetone completely, passed through strong cation exchange resin in H form and extracted with 220 gms of tri octyl amine. After extraction the amine layer containing tartaric acid was diluted with 5 parts of n-hexane per part of amine layer. Then to this mixture 1.25 parts of water per part of amine layer was added. Then, extraction of tartaric acid was done in aqueous layer at 55° C. in three stages. The aqueous layer was collected and activated carbon was then added. The mixture was stirred vigorously and filtered to obtain a clear solution. Then the solution was passed through a macroporous absorbent of the type Rohm & Haas XAD7 or its equivalent. Then the resulting tartaric acid solution was vacuum dried at 55° C. to yield 36 gms tartaric acid.

The aqueous solution of raffinate obtained after extraction of tartaric acid with trioctyl amine was given stream treatment for 20 min. The activated carbon was then added, the mixture stirred vigorously and filtered to obtain a clear solution. Then the solution was passed through strong anion exchange resin in OH from and then concentrated by vacuum evaporation to a sugar content of 65%.

The main advantages of the process of the sequential recovery of potassium bitartrate, pectin, tartaric acid and fruit sugar described in this invention are: (1) It enables recovery of four products of commercial value from tamarind pulp. (2) The sequence of recovery of each product is such that it simplifies the recovery of subsequent product recovered. (3) Each product is obtained in high purity as to meet the needs of the food and pharmaceutical industry. (4) Recovery of four products makes the process economically attractive. (5) It recovers tartaric acid directly as 10% aqueous solution from amine phase, enabling considerable savings in energy required for the recovery of the tartaric acid. (6) In comparison to the conventional route of extraction of tartaric acid, from wine argols which generates calcium sulfate as a waste product, the present process generates no by products. (7) The process makes the use of tertiary amine for thee extraction of tartaric acid from aqueous solution, and does not make use of chlorinated or any other carrier solvents. This eliminates the need for solvent recover, simplifies the process and makes it more environment friendly.

We claim:

1. A process for the recovery of potassium bitartrate, pectin, tartaric acid, and fruit sugar from tamarind pulp which comprises the steps of:

i) extracting tamarind pulp using 1:1 to 1:8 volumes of water at a temperature in the range of 25 to 100° C. in any conventional stirred vessel equipment for about 0.5–6 hrs to obtain a mixture of tartaric acid, potassium bitartrate, pectin and fruit sugar in aqueous medium in a quantitative manner;

ii) separating the residue from the pulp extract, treating the aqueous extract with a decolourising agent, for a period in the range of 10 mins to 90 mins at a temperature in the range of 20° C. to 80° C., stirring the mixture for 0.5 to 2 hrs at a temperature in the range of 20° C.–50° C., further treating the aqueous extract with decolourising agent and filtering it to remove the colouring matter, separating and concentrating the filtrate to recover the maximum amount of potassium bitartrate, concentrating the filtrate further to reduce the volume to ½ to 1/10th of the original volume, at a temperature in the range of 60° to 90° C. under reduced pressure, cooling the concentrated pulp allowing the concentrated pulp to stand to bring about complete separation of potassium bitartrate and subsequently purifying potassium bitartrate by recrystallization;

iii) treating the mother liquor obtained in step (ii) with an organic solvent to precipitate pectin, purifying the resultant pectin by repeated washing with acidified solvent;

iv) evaporating the solvent from both the filtrate and pectin washings obtained from step (ii), treating said filtrate with a cation exchange resin in H form, and extracting the eluate with a tertiary amine, separating the amine layer containing tartaric acid and diluting with a diluent and water and simultaneously heating the mixture at a temperature in the range of 50° C.–80° C., allowing the aqueous layer to separate and recovering the aqueous layer containing tartaric acid, treating with a decolourising agent under constant stirring for a time in the range of 10 to 60 mins, passing the filtrate through a microporous adsorbent of the type Rohm and Haas XAD 7 or its equivalent, evaporating the solvent and drying the aqueous solution to obtain solid tartaric acid, and v) injecting an aqueous raffinate solution obtained from step (iv), which is rich in fruit sugar and containing small amounts of tartaric acid with steam for a period in the range of 5 to 40 mins, treating with decolourising agent, removing the decolourising agent and passing the filtrate over an anion exchange resin, concentrating the eluate obtained from the column under vacuum at a temperature in the range of 55–60° C. to yield an aqueous solution of fruit sugar.

2. A process as claimed in claim 1 wherein, the water used for extracting the tamarind pulp is natural water, distilled water, or demineralised water.

3. A process as claimed in claim 1 wherein, the decolourising agent used is sulphur dioxide, sodium hydrosulphite or, activated carbon, in a quantity in the range of 0.5 to 5.0% of the aqueous solution of tartaric acid.

4. A process as claimed in claim 1 wherein, the solvent used in step (iii) for precipitating the pectin is methanol, ethanol, isopropanol, acetone, or methyl ethyl ketone, or mixtures of acetone and water or methyl ethyl ketone and water, wherein the ratio between acetone and water or methyl ethyl ketone and water is in the range from 90:10 to 98:2, respectively.

5. A process as claimed in claim 1 wherein, the acidified solvent used to wash the pectin is selected from methanol, ethanol, isopropanol, acetone, methyl ethyl ketone or with methanol, ethanol, isopropanol, acetone, methyl ethyl ketone containing no free acid or with mixture of water with either methanol, ethanol, isopropanol, acetone or methyl ethyl ketone.

6. A process as claimed in claim 1 wherein, the tertiary amine used is trioctylamine, tridecylamine, trilauryl amine or mixtures thereof, and the ratio of tertiary amine to tartaric acid in step (iv) used is in the range of 0.5 to 6 moles.

7. A process as claimed in claim 1, step iv), wherein the tertiary amine is directly used for the extraction of the tartaric acid.

8. A process as claimed in claim 1 wherein the mixture comprising tertiary amine, water, tartaric acid and hexane is heated up to 70° C.

9. A process as claimed in claim 1 wherein, the ratio of the diluent used in step (iv) to the amine layer is in the range of 3 to 10, parts of n-hexane per part of amine layer by volume and with 0.25 to 4 parts of water per part of amine layer in one to three stages.

10. The process according to claim 1, wherein in step (iv), said diluent is n-hexane.

* * * * *